United States Patent [19]

Quarfoot

[11] Patent Number: 4,759,354
[45] Date of Patent: Jul. 26, 1988

[54] WOUND DRESSING

[75] Inventor: Alan J. Quarfoot, Palatine, Ill.

[73] Assignee: The Kendall Company, Boston, Mass.

[21] Appl. No.: 935,427

[22] Filed: Nov. 26, 1986

[51] Int. Cl.⁴ ............................................. A61L 15/00
[52] U.S. Cl. ..................................... 128/156; 128/155;
604/368; 106/124; 424/81; 428/423.4
[58] Field of Search ................. 128/155, 156, DIG. 8,
128/; 604/368, 897, 892, 894; 106/124, 125;
424/81, 424; 428/319.3, 423.4; 530/356

[56] References Cited

U.S. PATENT DOCUMENTS

| | | | |
|---|---|---|---|
| 446,610 | 2/1891 | Osgood | 128/155 |
| 3,157,524 | 11/1964 | Artandi | 128/DIG. 8 |
| 3,425,412 | 2/1969 | Pope | 128/156 |
| 3,800,792 | 4/1974 | McKnight et al. | 128/156 |
| 4,242,242 | 12/1980 | Allen | 604/368 |
| 4,294,241 | 10/1981 | Miyata | 128/156 |
| 4,390,519 | 6/1983 | Sawyer | 128/156 |
| 4,538,603 | 9/1985 | Pawelchak et al. | 128/156 |
| 4,619,253 | 10/1986 | Anhauser et al. | 128/156 |
| 4,655,767 | 4/1987 | Woodard et al. | 604/896 |

Primary Examiner—Richard J. Apley
Assistant Examiner—Paul Prebilic
Attorney, Agent, or Firm—Alvin Isaacs

[57] ABSTRACT

Novel wound dressings comprising the following essential elements, in order:

a thin outer vapor-permeable layer; an absorbent adhesive layer for adhering the wound dressing to the skin and for acting as a reservoir for wound exudate; and a layer of collagen for placement directly on the wound, said collagen layer being of smaller dimensions than said absorbent adhesive layer whereby areas of said absorbent adhesive layer extending beyond the periphery of said collagen layer can be applied to the skin surrounding the wound.

11 Claims, 2 Drawing Sheets

WOUND DRESSING

BACKGROUND OF THE INVENTION

In general, dressings to be applied to various types of wounds, including burns and the like, should ideally promote healing, and provide protection, e.g. a bacterial barrier against infection, and prevent pooling of wound exudate. While of lesser importance, they should also be as comfortable as possible and not cause or contribute to ancillary problems such as bed sores and the like which are common with patients bedridden for extended periods of time following surgery or treatment for burns and/or inflicted wounds. Moreover, they should ideally be transparent for visualization and monitoring of the underlying wound.

For convenience, such products will be referred hereinafter throughout the specification and claims simply as "wound dressings".

While wound dressings are known in the art which will provide some of the above-noted desired properties, prior to the present invention the need for an improved wound dressing more closely approximating the above criteria still exists.

For example, the patent literature is replete with references to various types of wound dressings, including dressings employing hydrogel layers to absorb wound exudate. Nevertheless, at present there are essentially only two types of wound dressings commercially available, each of which affords certain advantages but also suffers from certain disadvantages.

The first such commercially available product is a hydrogel such as "Vigilon" (trademark of C. R. Bard, Inc. for a non-adherent, breathable, moist hydrogel which is inert, 96% water and 4% polyethylene oxide.) The Vigilon hydrogel provides a moist environment conducive to wound healing and granulation tissue formation as well as the absorption of wound exudate which should be inherent in the function of hydrogels in general. However, it is not highly absorbent and consequently requires fairly frequent replacement to obviate pooling of exudate and related problems. Moreover, since it is non-adherent to intact skin, it requires use of adhesive tape for application to the skin as well as applying gauze or other covering means to prevent escape of the exudate. Apart from the time, trouble and expense of storing and assembling the materials needed to complete the wound dressing, bulky bandages frequently result, particularly where the wound covers a large or irregular surface. This in turn may contribute to the further discomfort of the patient as well as bedsores from the chafing and rubbing. Hydrogels such as Vigilon are disclosed, for example, in U.S. Pat. Nos. 3,419,006; 3,664,343; and 3,993,551.

For these and perhaps other reasons, a more commonly used product for wound dressings is "Duo-DERM" (trademark of E. R. Squibb & Sons, Inc. for a dressing containing moisture reactive particles surrounded by an inert, hydrophobic polymer.) The Duo-DERM dressing has an adhesive inner surface for application to the skin and wound and is said to be virtually impermeable to oxygen. As moisture enters the dressing, the moisture-reactive particles gradually swell and dissolve to contain the accumulating exudate.

Wound dressings of the DuoDERM structure afford certain advantages, chief of which are the fact they are unitary structures including the adhesive layer for securing the dressing, ease of application and the ability to contain exudate.

However, they possess certain significant disadvantages as well, e.g. the adhesive layer is a barrier to diffusion of exudate from the wound so that most of the fluid never diffuses through the adhesive layer; no transpiration of fluid through the impermeable outer surface; the adhesive is aggressive to the intact perilesional skin so that on removal this skin may be traumatized; loss of adhesion in a day or two due to fluid accumulation; tendency to exhibiting an unpleasant odor when dissolved in wound fluid; and the oxygen-free environment provided by the oxygen- and water-impermeable outer surface provides a favorable environment at the wound locus for the growth of harmful anaerobic bacteria.

The above two products are, in applicant's judgement, fairly representative of commercially available wound dressings. Others of course do exist.

It is also known in the art to employ collagen in wound dressings. Illustrative patents pertaining thereto will be discussed subsequently in the "Detailed Description of the Invention".

In general, it can be said that it has long been known that some types and/or forms of collagen promote wound healing and may accordingly be employed in wound dressings. However, they lack the absorbency capacity of hydrogels and, apparently for this reason, are not known to be employed in commercially available wound dressings.

As previously stated, the patent literature contains numerous references to wound dressings, particularly dressings employing hydrogels.

While not intended to be a complete survey of the state of the art pertaining thereto, the following additional patents are nevertheless illustrative: 3,249,109; 4,153,055; 4,347,841; 4,367,732; 4,438,258; 4,516,571; 4,541,426; 4,552,138; and 4,556,056.

As was also previously stated, a wound dressing should ideally promote healing, provide protection against infection, minimize pooling of wound exudate yet allow subsequent aspiration, be as comfortable as possible and not contribute to wound trauma on removal, etc. Moreover, they should preferably be easy to apply. At present, there are no available wound dressings providing all of the above functions.

The task of the present invention may accordingly be said to be to provide a wound dressing which satisfies the above-mentioned criteria in a composite structure which is both easy to apply and also contains all of the components essential for application and retention of the dressing to the skin.

BRIEF DESCRIPTION OF THE INVENTION

In accordance with this invention a wound dressing is provided utilizing the "wound friendly" properties of collagen in combination with an absorbent adhesive layer for adhering the dressing and for acting as a reservoir for wound exudate, the dressing further having an oxygen- and vapor-permeable backing which permits transpiration to ambient air as well as precluding an anaerobic environment favorable to bacteria.

Preferably, the absorbent adhesive layer comprises an adhesive hydrogel.

DETAILED DESCRIPTION OF THE INVENTION

Figure 1:
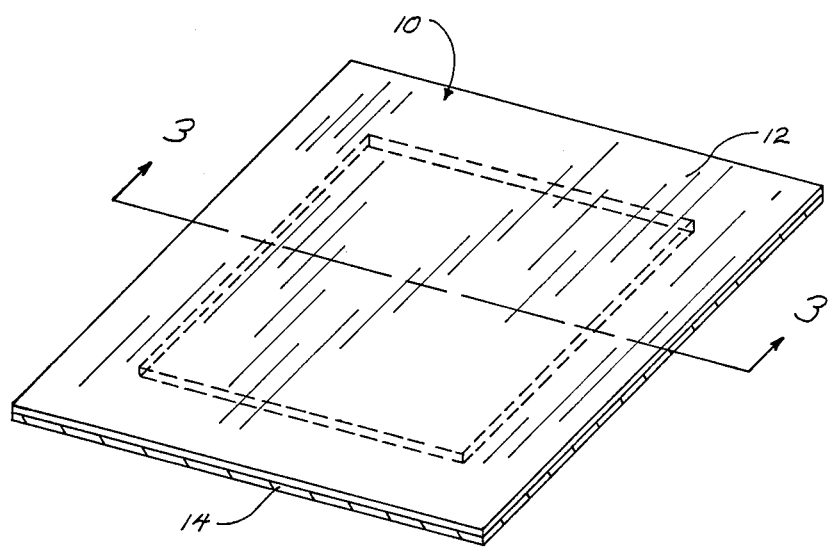
FIG. 1 is a perspective view showing the top or outer surface of the wound dressing.
Figure 2:
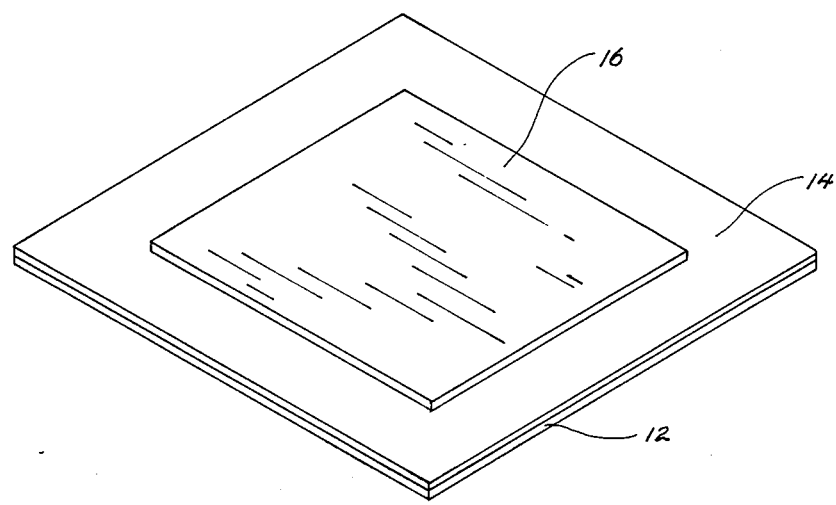
FIG. 2 is a perspective view showing the bottom or surface of the wound dressing adapted to be placed on the skin and to cover the wound.

As is well known, collagen, a major constituent of various structures rich in dense connective tissue, e.g dura mater, fascia, intestine (catgut) or tail tendons, has been used as a natural product in various applications in surgery for about a century. Collagen films, membranes, tapes, sponges and felts have heretofore been used clinically for wound dressings and other purposes.

One particularly useful physical form of collagen for wound dressings is a sponge or foam, e.g. a highly crosslinked collagen sponge.

Although collagen can be prepared by enzymatic digestion, non-enzymatic procedures are preferred because they are less expensive and do not disrupt the fibrillar structure of collagen. This may be accomplished, for example, by successive extraction of homogenized collagen-rich tissue (e.g. bovine skin or Achilles tendon) with alkali and acids. The sponge may be prepared from the pure collagen by known techniques.

By way of illustration, pure collagen, partially swollen at acid pH, may be dispersed in an aqueous medium to form a slurry. The resulting thoroughly mixed gel-like dispersion is then poured into trays and frozen. From this state, it is dehydrated by lyophilization or by extraction with organic solvents. The resulting sponge is then crosslinked, e.g. with formaldehyde vapor, to stabilize the three-dimensional meshwork. [Without crosslinking, the collagen sponge, upon contact with fluids, collapses and forms a gel at the fluid boundary. Crosslinked collagen sponge, on the other hand, is resilient and when compressed in contact with water expands to its original size and shape.]

Irrespective of the form, it is known that collagen as a substrate favors cell growth and is very useful for wound and burn dressings.

As reported, for example, by Milos Chvapil in "Collagen Sponge: Theory and Practice of Medical Applications" appearing in J. Biomed. Mater. Res., Vol. 11, pp. 721–741 (1977), collagenous materials had several beneficial effects as dressings. A dressing of reconstituted collagen film afforded excellent protective coverage over large areas of excised skin or third degree burns for three to four weeks, exhibiting diminished fluid loss and helping to maintain sterility. In burn studies, the collagen was found equal to autogenous skin grafts in diminishing fluid loss, maintaining sterility and promoting healing. In studies on treating pressure sores in paraplegic patients with collagen sponge, the clinicians noted the following: (1) wounds were clean and bacterial infection retarded; (2) drainage of wound secretion was diminished; (3) formation of new granulation tissue was improved; (4) undermined edges of the pressure sores were closed; (5) formation of the epithelium was stimulated; (6) closed wounds showed no contractures; (7) moist pressure sore fissures which showed no tendency to heal were closed; (8) no immunological reactions toward collagen were observed: and (9) the general condition of the patient was improved. Other studies reported in this article are also favorable to the use of collagen as a dressing for wounds and burns and need not be discussed herein.

The patent literature also contains many references to the use of collagens as wound dressings.

Figure 3:
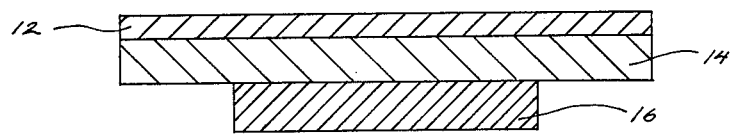
FIG. 3 is an edge sectional view taken along lines 3—3 of FIG. 1.

For example, U.S. Pat. No. 3,800,792 issued to McKnight discloses (FIG. 3) a dressing having a moisture vapor-permeable outer film to which is laminated a compressed collagen foam layer containing collagen fibers and particles of silver metal. U.S. Pat. Nos. 3,491,760; 3,471,598 and 2,202,566 cited in Col. 2 of McKnight also relate to dressings including collagen.

U.S. Pat. No. 4,294,241 issued to Miyata relates to skin or wound dressings prepared in gel or sheet form from enzyme-solubilized collagen and/or such chemically modified collagen. These collagen skin dressing are said to have the following properties: good adherence to wound surface and acceleration of epithelialization; prevention of loss of protein, fluid or electrolytes; prevention of infection; reduction of pain; long-term preservation capability; and no stimulation of local tissue response.

U.S. Pat. No. 4,438,258, which relates to specified hydrogels states, in the Description of the Prior Art, that hydrogels have already been indicated for use as a wound dressing but these have generally been natural and semi-synthetic products such as collagen, gelatin and starch products.

U.S. Pat. No. 4,570,629 issued to Widra relates to hydrophilic bipolymeric copolyelectrolytes comprising a water-soluble linear anionic protein polyelectrolyte component derived from keratin and a water-soluble cationic biopolymer polyelectrolyte component derived from collagen and/or a glucosaminoglycan. Hydrogel membranes formed from these copolyelectrolytes are said to be useful as biodegradable dressings for denuded tissue wound sites. It is stated by the patentee that the membranes are strongly adherent to underlying tissue, highly permeable to oxygen, absorbent to wound exudate, have water vapor transport characteristics sufficient to keep the underlying tissue moist without creating pooling, and have intact bacterial barrier characteristics. Although thicknesses of at least one mil are stated to be sufficient to most applications, it is further stated that thicknesses of about 1–7 mils are particularly suitable. While the patented membranes do provide many characteristics required for wound dressings, they possess certain disadvantages, chief of which are the strong adherence to wound tissue which can cause trauma on removal; require tape, gauze and the like to complete the dressing; and inadequate absorption of exudate to prevent pooling of at least major or deep wounds. In the last mentioned context, it will be noted that, while the patentee speaks of preventing pooling, the patented membranes are too thin to absorb the requisite amounts of moisture and the patent does not teach how to prepare nor have applicant's been able to prepare layers of sufficient thickness for this purpose.

By way of recapitulation, collagen alone or in combination with other substances have been applied as wound dressings directly to the wound tissue. While various forms of collagen, e.g. films, foams or sponges have been well documented as being materials which promote healing while protecting the wound, they lack the water-absorptive properties to prevent pooling of exudate.

On the other hand, hydrogels are known to absorb large quantities of moisture. However, they generally fall into one of two categories:

(1) those such as the aforementioned "Vigilon" which are only moderately absorbent but which are generally regarded as wound friendly; and (2) those, including adhesive hydrogels such as "EnerTac" NDO gel (trademark of Medtronic, Inc.) and other acrylic based hydrogels which possess good absorptive properties but are not wound friendly or, at best, do not possess the wound friendly properties of collagen.

The present invention in essence can be said to be predicated upon the concept of providing a unitary or composite wound dressing having the adhesive properties for adherence to the skin and which utilizes the properties of collagen along with the water-absorptive properties of materials such as hydrogels, the wound dressing further having an outer oxygen- and vapor-permeable film which will permit transpiration of fluid diffusing through the hydrogel or other absorbent material, while preventing drying of the dressing by ambient air.

Specifically, the novel dressings of this invention will comprise a thin outer oxygen- and vapor-permeable film; a layer of an absorbent adhesive for adhering the wound dressing to the skin and for acting as a reservoir for wound exudate absorbed therein; and a layer of collagen adapted for placement directly on the wound, the collagen layer being of smaller dimensions than the absorbent adhesive layer whereby areas of the adhesive layer extending beyond the periphery of the collagen layer can be applied to the skin surrounding the wound to adhere the dressing in place.

The invention will be further understood by reference to the accompanying drawing.

As shown therein, dressing 10 comprises oxygen- and vapor-permeable film or layer 12, absorbent adhesive layer 14 and collagen layer 16 of smaller dimensions and which, as shown, is centrally positioned on the absorbent adhesive layer.

Layer 12, which further serves as a bacterial barrier, is preferably transparent. It is preferably as thin as possible, e.g. on the order of one mil thick, but may be thicker if desired. As examples of useful materials for layer 12, mention may be made of polyurethanes, e.g.'-'Pellethane" (trademark of Upjohn for a polyether polyurethane), "Pebax" (trademark of ATOCHEM Inc. for a polyether block polyamide), etc.; polymers such as "Hytrel" (trademark of duPont for a copolyether-ester polymer comprising butylene terephthalate segments and polyalkylene ether glycol segments) and the like.

If found desirable or expedient to do so or if dressing 10 does not possess the requisite dimensional stability for handling and application, a removable support sheet, e.g. an oxygen- and vapor-impermeable sheet material (not shown) such as ethylene vinyl acetate may be releasably secured to the outer surface of the dressing. In this event, it will be appreciated that this removable sheet will be peeled away following application to permit transpiration of moisture from the outer surface of the hydrogel layer.

Adhesive layer 14 may be any of the per se known synthetic or naturally occurring absorptive material which exhibit the requisite aggressiveness or tackiness for adherence to the skin. Preferably, they are hydrogels and, more particularly, the class of hydrogels which are characterized as being capable of having the capacity to absorb relatively large amounts of liquids. As examples of per se known hydrogels which may be employed, mention may be made of those comprising a copolymer of 2-acrylamido-2-methylpropane sulfonic acid or a salt thereof which are described in, for example, in U.S. Pat. Nos. 4,391,278 or 4,242,242, or Canadian Pat. Nos. 1,173,114, 1,173,116 or 1,173,115, all assigned to Medtronic; the hydrogels commercially available from Medtronic, Inc. under the trademarks "EnerTac" NDO Gel and "EnerTac" HH Gel, etc. However, absorbent materials other than hydrogels are also contemplated for use in the present invention. Such useful materials include adhesive hydrocolloids, e.g. "Hydroactive" (trademark of E. R. Squibb & Sons for the absorbent/adhesive employed in the aforementioned DuoDERM dressing); and the like.

Absorbent layer 14 should be of sufficient thickness to provide the required absorption (and subsequent transpiration) of wound exudate and may, for example, be on the order of 50 to 150 mils thick. It will, however, be appreciated that the thickness of absorbent layer 14 will in part be dependent upon its absorptive capacity and will in part be dependent upon the amount of exudate which need be absorbed by the dressing in the contemplated usage.

Accordingly, it is not capable of precise quantification and the foregoing thicknesses, i.e. 50 to 150 mils are to be taken as typical. Thinner or thicker layers are therefore also contemplated. In any event, the selection of the particular thickness will be within the expected judgement of the skilled worker in the light of the foregoing discussion.

Collagen layer 16 may comprise any of the known collagens, including those heretofore discussed and which have previously been employed in wound dressings. Preferably, however, it is a film or sponge (foam) which may either be crosslinked or non-crosslinked depending upon whether the clinician wishes for the collagen layer to retain its integrity or become a gel upon contact with liquid, as previously discussed. Suitable materials for collagen layer 16 include "COLLA-STAT" (trademark of The Kendall Company for an absorbable collagen hemostatic sponge); "Hemopad" (trademark of ASTRA for an absorbable hemostat); "Helistat" (trademark of American Biomaterials Corp.) etc.

The thickness of collagen layer 16 is not critical and may vary over a wide range. It should, however, preferably be at least 5 mils thick. It will be appreciated that collagen foams, for example, are appreciably thicker, e.g. greater than 50 mils. In any event, as discussed above with respect to layer 14, the selection of the particular collagen, its physical form and its thickness will all be within the expected judgement of the skilled worker.

The following example shows by way of illustration and not by way of limitation the practice of this invention.

EXAMPLE

A wound dressing of the configuration shown in the drawings was prepared as follows. A sterile layer of "EnerTac" NDO gel approximately 2.5 inches×2.5 inches was adhered to one surface of a "Pellethane" No. 2363-80AE urethane film of approximatley the same linear dimesions. A "Collstat" sponge approximately 0.3 cm thick (about 118 mils) measuring about 1.5 inches×1.5 inches was then centrally positioned on the free surface of the NDO adhesive hydrogel, leaving about 0.5 of an inch of adhesive surface around the periphery of the dressing to the skin. In accordance with conventional test procedures, a wound approximately 1.5 cm×1.5 cm was made on a pig. After achieving hemostasis, the wound was covered with the above dressing so that the collagen layer completely covered the wound. The dressing was removed, the wound examined and a similar new dressing then applied at 48 to 72 hour intervals. At the end of three weeks, the wound was removed by wide excision, fixed in formalin and subjected to histologic examination.

Both gross observation and histologic results confirmed the great efficacy of the wound dressing. The wound was found to have closed rapidly and in unremarkable manner with the reestablishment of normal tissue architecture. By day 8 the wound had contracted to 10 mm×10 mm and possessed a normal bed of granulation tissue. The wound closed further to 6 mm×6 mm by Day 11. After Day 18, the wound was no longer dressed since it had obviously closed and an intact epidermis had been reestablished. The histopathology report confirmed the visual observation that the wound had healed, as well as the mature nature of the tissue. Only a very small scar was observed and the new tissue was characterized as exhibiting a uniformly colored pigmentation.

Microscopic findings of the tissue were as follows:
No scab present,
epithelial covering complete,
only slight congestion and fibrous tissue,
fibroblast proliferation moderate,
inflammatory infiltration and granulomatous reaction minimal,
minimal eosinophilic deposits,
primary cell type is lymphoid, and
pigment and macrophages present.

From the foregoing description and illustrative example it will be seen that the present invention provides an elegant and highly efficaceous composite wound dressing containing all of the requisite components for covering the wound and adherence to the skin. The novel dressing is further characterized as being extremely wound friendly, a property known to be inherent in the application of collagen to the wound, while at the same time permitting absorption of exudate and subsequent transpiration of moisture to the ambient air through the outer oxygen- and moisture-permeable surface, which surface further serves to provide a barrier to bacteria.

It will, however, be appreciated that the novel dressing is capable of various modifications without departing from the scope of the invention herein described. Various layers or components performing specific desired functions may be added. For example, the dressing may be provided initially with a removable impermeable backing to facilitate handling as well as to preclude drying out of the essential layers during storage. If found desirable or expedient to do so, a release sheet of the type well known in the adhesive art, e.g. silicone paper, may be applied over the free surface of the absorptive adhesive in order to preclude premature adhesion. It is further contemplated that a release system for the controlled administration of a medicament or other bioactive agent may be incorporated in the dressing for treatment of the wound.

Since certain changes can be made without departing from the scope of the invention herein described, it is intended that all matter contained in the foregoing description, including the drawings and example, shall be taken as illustrative and not in a limiting sense.

I claim:

1. A wound dressing for preventing pooling of wound exudate and for promoting healing comprising, in order, the following essential elements:
    an outer oxygen- and vapor-permeable layer permitting transpiration of liquid from said dressing;
    an intermediate layer having an adhesive capability for adhering the dressing to the skin and an absorbent capacity for wound exudate;
    and a layer consisting essentially of collagen for promoting healing adapted to be placed directly on the wound, said collagen layer being of smaller dimensions than said intermediate layer, whereby adhesive portions of said intermediate layer extending beyond the periphery of said collagen layer are exposed for adhering said dressing.

2. A wound dressing as defined in claim 1 wherein said collagen is in the form of a sponge or film.

3. A wound dressing as defined in claim 1 wherein said intermediate layer comprises an adhesive hydrogel or hydrocolloid.

4. A wound dressing as defined in claim 3 wherein said collagen layer is substantially centrally positioned with respect to said intermediate layer of greater dimensions.

5. A wound dressing as defined in claim 1 including a removable vapor impermeable sheet material releasably secured to the outer surface of said oxygen- and vapor-permeable layer.

6. A wound dressing combining the wound friendly healing capability of collagen with the anti-pooling capacity of an absorbent material and a dressing surface permitting transpiration of fluid from said dressing, said dressing comprising, in order the following essential elements:
    a thin oxygen- and vapor-permeable layer permitting transpiration of fluid from said dressing;
    an absorbent adhesive layer comprising an adhesive hydrogel or hydrocolloid adapted to absorb wound exudate and for adhering said dressing to the skin;
    and a layer consisting essentially of collagen, said collagen layer having smaller dimensions than said absorbent adhesive layer, leaving portions of said adhesive layer extending beyond the periphery of said collagen layer free for adhering said dressing to the skin.

7. A wound dressing as defined in claim 6 wherein said absorbent adhesive comprises a hydrogel of the class characterized as having the capacity to absorb large amounts of liquid.

8. A wound dressing as defined in claim 7 wherein said hydrogel comprises a polymer of 2-acrylamido-2-methylpropane sulfonic acid or a salt thereof.

9. A wound dressing as defined in claim 6 wherein said collagen layer is in the form of a sponge.

10. A wound dressing as defined in claim 9 wherein said collagen sponge layer is greater than 50 mils thick.

11. A wound dressing as defined in claim 6 wherein said absorbent adhesive layer is from about 50 to about 150 mils thick.

* * * * *